(12) United States Patent
Focht et al.

(10) Patent No.: US 9,416,775 B2
(45) Date of Patent: Aug. 16, 2016

(54) INTERNAL CAM METERING PUMP

(71) Applicant: Becton Dickinson and Company, Franklin Lakes, NJ (US)

(72) Inventors: Kenneth Focht, Needham, MA (US); Joseph Gordon, Mansfield, MA (US); Justin Fisk, Providence, RI (US); Matthew J. Perry, East Greenwich, RI (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 65 days.

(21) Appl. No.: 14/322,432

(22) Filed: Jul. 2, 2014

(65) Prior Publication Data

US 2016/0000999 A1    Jan. 7, 2016

(51) Int. Cl.

| | |
|---|---|
| *F04B 7/06* | (2006.01) |
| *F04B 7/04* | (2006.01) |
| *F04B 7/00* | (2006.01) |
| *F04B 9/04* | (2006.01) |
| *F04B 19/00* | (2006.01) |
| *F04B 39/08* | (2006.01) |
| *A61M 5/142* | (2006.01) |
| *A61M 5/14* | (2006.01) |
| *F04B 43/04* | (2006.01) |
| *A61M 5/168* | (2006.01) |

(52) U.S. Cl.
CPC .............. *F04B 7/06* (2013.01); *A61M 5/14216* (2013.01); *A61M 5/16831* (2013.01); *F04B 7/0057* (2013.01); *F04B 7/0065* (2013.01); *F04B 7/04* (2013.01); *F04B 9/042* (2013.01); *F04B 19/006* (2013.01); *F04B 39/08* (2013.01); *A61M 5/1413* (2013.01); *A61M 5/14244* (2013.01); *A61M 2005/14252* (2013.01); *A61M 2005/16863* (2013.01); *A61M 2205/103* (2013.01); *F04B 9/047* (2013.01); *F04B 43/043* (2013.01)

(58) Field of Classification Search
CPC ............ A61M 5/142; A61M 5/14212; A61M 5/14216; A61M 5/1422; A61M 2005/14533; F04B 7/0057; F04B 7/0061; F04B 7/0065; F04B 7/0069; F04B 7/06; F04B 9/025; F04B 9/04; F04B 9/042; F04B 9/045; F04B 9/047; F04B 19/006; F04B 7/0042; F04B 7/0046; F04B 7/0053; F04B 7/04; F04B 39/08

See application file for complete search history.

(56) References Cited

U.S. PATENT DOCUMENTS 2,821,926 A * 2/1958 Miller ........................ F04B 9/02
                                                    192/78
3,510,235 A * 5/1970 Bensinger ............... F04B 19/02
                                                   417/462

(Continued)

FOREIGN PATENT DOCUMENTS

| EP | 0980687 A2 | 2/2000 |
|---|---|---|
| EP | 1044374 B1 | 10/2008 |

(Continued)

*Primary Examiner* — Bhisma Mehta
*Assistant Examiner* — James D Ponton
(74) *Attorney, Agent, or Firm* — Dickinson Wright PLLC

(57) ABSTRACT

A micropump according to the invention uses an eccentric cam member rotating within a pump housing to sequentially open and close valves in the pump housing to withdraw fluid from a reservoir and provide metered amounts of the fluid to a cannula port for administration to a patient. The micropump may be used in a disposable pump for continuous infusion of medication such as insulin.

15 Claims, 14 Drawing Sheets

(56) References Cited

U.S. PATENT DOCUMENTS

| | | | |
|---|---|---|---|
| 3,857,382 A | 12/1974 | Williams, Jr. et al. |
| 3,963,380 A | 6/1976 | Thomas, Jr. et al. |
| 4,204,538 A | 5/1980 | Cannon |
| 4,417,860 A | 11/1983 | Justice |
| 4,465,478 A | 8/1984 | Sabelman |
| 4,479,759 A | 10/1984 | Zeitz |
| 4,685,902 A | 8/1987 | Edwards et al. |
| 4,723,947 A | 2/1988 | Konopka |
| 4,734,092 A | 3/1988 | Millerd |
| 4,755,173 A | 7/1988 | Konopka et al. |
| 5,002,528 A | 3/1991 | Palestrant |
| 5,176,662 A | 1/1993 | Bartholomew et al. |
| 5,226,899 A | 7/1993 | Lee et al. |
| 5,257,980 A | 11/1993 | Van Antwerp et al. |
| 5,279,585 A | 1/1994 | Balkwill |
| 5,279,586 A | 1/1994 | Balkwill |
| 5,312,233 A * | 5/1994 | Tanny .................. F04B 7/0038 417/316 |
| 5,453,099 A | 9/1995 | Lee et al. |
| 5,494,420 A * | 2/1996 | Mawhirt .................. F04B 7/06 417/499 |
| 5,522,803 A | 6/1996 | Teissen-Simony |
| 5,536,249 A | 7/1996 | Castellano et al. |
| 5,545,143 A | 8/1996 | Fischell |
| 5,545,152 A | 8/1996 | Funderburk et al. |
| 5,549,575 A | 8/1996 | Giambattista |
| 5,569,214 A | 10/1996 | Chanoch |
| 5,582,598 A | 12/1996 | Chanoch |
| 5,593,390 A | 1/1997 | Castellano et al. |
| 5,674,204 A | 10/1997 | Chanoch |
| 5,728,074 A | 3/1998 | Castellano et al. |
| 5,820,602 A | 10/1998 | Kovelman et al. |
| 5,851,197 A | 12/1998 | Marano et al. |
| 5,858,001 A | 1/1999 | Tsals et al. |
| 5,858,005 A | 1/1999 | Kriesel |
| 5,921,966 A | 7/1999 | Bendek |
| 5,925,021 A | 7/1999 | Castellano et al. |
| 5,944,700 A | 8/1999 | Nguyen |
| 5,957,895 A | 9/1999 | Sage et al. |
| 5,957,896 A | 9/1999 | Bendek |
| 5,968,011 A | 10/1999 | Larsen et al. |
| 5,980,506 A | 11/1999 | Mathiasen |
| 6,017,328 A | 1/2000 | Fischell et al. |
| 6,056,718 A | 5/2000 | Funderburk et al. |
| 6,068,615 A | 5/2000 | Brown et al. |
| 6,074,369 A | 6/2000 | Sage et al. |
| 6,086,575 A | 7/2000 | Mejslov |
| 6,093,172 A | 7/2000 | Funderburk et al. |
| 6,096,010 A | 8/2000 | Walters |
| 6,110,148 A | 8/2000 | Brown et al. |
| 6,110,149 A | 8/2000 | Klitgaard |
| 6,123,690 A | 9/2000 | Mejslov |
| 6,132,400 A | 10/2000 | Waldenburg |
| 6,175,752 B1 | 1/2001 | Say et al. |
| 6,221,053 B1 | 4/2001 | Walters |
| 6,248,095 B1 | 6/2001 | Giambattista |
| 6,254,586 B1 | 7/2001 | Mann et al. |
| 6,272,364 B1 | 8/2001 | Kurnik |
| 6,275,717 B1 | 8/2001 | Gross et al. |
| 6,277,099 B1 | 8/2001 | Strowe |
| 6,277,627 B1 | 8/2001 | Hellinga |
| 6,293,925 B1 | 9/2001 | Safabash et al. |
| 6,302,866 B1 | 10/2001 | Marggi |
| 6,352,523 B1 | 3/2002 | Brown et al. |
| 6,355,021 B1 | 3/2002 | Nielsen et al. |
| 6,391,005 B1 | 5/2002 | Lum et al. |
| 6,485,461 B1 | 11/2002 | Mason et al. |
| 6,520,938 B1 | 2/2003 | Funderburk et al. |
| 6,521,446 B2 | 2/2003 | Hellinga |
| 6,537,242 B1 | 3/2003 | Palmer |
| 6,544,212 B2 | 4/2003 | Galley et al. |
| 6,546,269 B1 | 4/2003 | Kurnik |
| 6,551,276 B1 | 4/2003 | Mann et al. |
| 6,558,351 B1 | 5/2003 | Steil et al. |
| 6,565,509 B1 | 5/2003 | Say et al. |
| 6,576,430 B1 | 6/2003 | Hsieh et al. |
| 6,579,267 B2 | 6/2003 | Lynch et al. |
| 6,582,404 B1 | 6/2003 | Kitgaard |
| 6,589,229 B1 | 7/2003 | Connelly et al. |
| 6,607,509 B2 | 8/2003 | Bobroff et al. |
| 6,656,158 B2 | 12/2003 | Mahoney et al. |
| 6,656,159 B2 | 12/2003 | Flaherty |
| 6,669,669 B2 | 12/2003 | Flaherty et al. |
| 6,692,457 B2 | 2/2004 | Flaherty |
| 6,692,472 B2 | 2/2004 | Hansen |
| 6,699,218 B2 | 3/2004 | Flaherty et al. |
| 6,706,159 B2 | 3/2004 | Moerman et al. |
| 6,723,072 B2 | 4/2004 | Flaherty et al. |
| 6,740,059 B2 | 5/2004 | Flaherty |
| 6,749,560 B1 | 6/2004 | Konstrorum et al. |
| 6,749,587 B2 | 6/2004 | Flaherty |
| 6,768,425 B2 | 7/2004 | Flaherty et al. |
| 6,830,558 B2 | 12/2004 | Flaherty et al. |
| 6,830,562 B2 | 12/2004 | Mogensen et al. |
| 6,840,922 B2 | 1/2005 | Nielsen et al. |
| 6,852,104 B2 | 2/2005 | Blomquist |
| 6,932,794 B2 | 8/2005 | Giambattista |
| 6,936,032 B1 | 8/2005 | Bush, Jr. |
| 6,945,961 B2 | 9/2005 | Miller |
| 6,949,084 B2 | 9/2005 | Marggi et al. |
| 6,960,162 B2 | 11/2005 | Saadat et al. |
| 6,960,192 B1 | 11/2005 | Flaherty et al. |
| 6,977,180 B2 | 12/2005 | Hellinga et al. |
| 6,997,907 B2 | 2/2006 | Safabash et al. |
| 7,004,928 B2 | 2/2006 | Aceti et al. |
| 7,018,360 B2 | 3/2006 | Flaherty et al. |
| 7,018,364 B2 | 3/2006 | Giambattista |
| 7,029,455 B2 | 4/2006 | Flaherty |
| 7,052,251 B2 | 5/2006 | Nason et al. |
| 7,064,103 B2 | 6/2006 | Pitner et al. |
| 7,070,580 B2 | 7/2006 | Nielsen |
| 7,083,597 B2 | 8/2006 | Lynch et al. |
| 7,104,972 B2 | 9/2006 | Moller |
| 7,109,878 B2 | 9/2006 | Mann et al. |
| 7,128,727 B2 | 10/2006 | Flaherty et al. |
| 7,137,964 B2 | 11/2006 | Flaherty |
| 7,144,384 B2 | 12/2006 | Gorman et al. |
| 7,169,132 B2 | 1/2007 | Bendek |
| 7,207,974 B2 | 4/2007 | Safabash et al. |
| 7,214,207 B2 | 5/2007 | Lynch et al. |
| 7,220,248 B2 | 5/2007 | Mernoe |
| 7,226,278 B2 | 6/2007 | Nason et al. |
| 7,250,037 B2 | 7/2007 | Shermer et al. |
| 7,303,543 B1 | 12/2007 | Maule et al. |
| 7,303,549 B2 | 12/2007 | Flaherty et al. |
| 7,310,544 B2 | 12/2007 | Brister et al. |
| 7,318,816 B2 | 1/2008 | Bobroff et al. |
| 7,329,239 B2 | 2/2008 | Safabash et al. |
| 7,354,420 B2 | 4/2008 | Steil et al. |
| 7,496,392 B2 | 2/2009 | Alarcon et al. |
| 7,678,079 B2 | 3/2010 | Shermer et al. |
| 7,722,595 B2 | 5/2010 | Pettis et al. |
| 7,726,955 B2 | 6/2010 | Ryser et al. |
| 7,857,131 B2 | 12/2010 | Vedrine |
| 8,021,334 B2 | 9/2011 | Shekalim |
| 8,282,366 B2 * | 10/2012 | Hilber ............... A61M 5/14244 417/420 |
| 2002/0040208 A1 | 4/2002 | Flaherty et al. |
| 2003/0055380 A1 | 3/2003 | Flaherty |
| 2003/0109829 A1 | 6/2003 | Mogensen et al. |
| 2003/0176852 A1 | 9/2003 | Lynch et al. |
| 2003/0199823 A1 | 10/2003 | Bobroff et al. |
| 2004/0002682 A1 | 1/2004 | Kovelman et al. |
| 2004/0010207 A1 | 1/2004 | Flaherty et al. |
| 2004/0059316 A1 | 3/2004 | Smedegaard |
| 2004/0078028 A1 | 4/2004 | Flaherty et al. |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0162521 A1 | 8/2004 | Bengtsson |
| 2004/0204673 A1 | 10/2004 | Flaherty |
| 2004/0204687 A1 | 10/2004 | Mogensen et al. |

(56) References Cited

U.S. PATENT DOCUMENTS

| | | |
|---|---|---|
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0043687 A1 | 2/2005 | Mogensen et al. |
| 2005/0065760 A1 | 3/2005 | Murtfeldt et al. |
| 2005/0090784 A1 | 4/2005 | Nielsen et al. |
| 2005/0101932 A1 | 5/2005 | Cote et al. |
| 2005/0101933 A1 | 5/2005 | Marrs et al. |
| 2005/0113761 A1 | 5/2005 | Faust et al. |
| 2005/0124936 A1 | 6/2005 | Mogensen et al. |
| 2005/0171512 A1 | 8/2005 | Flaherty |
| 2005/0182366 A1 | 8/2005 | Vogt et al. |
| 2005/0197625 A1 | 9/2005 | Haueter |
| 2005/0203461 A1* | 9/2005 | Flaherty ............ A61M 5/14248 604/131 |
| 2005/0215982 A1 | 9/2005 | Malave et al. |
| 2005/0222645 A1 | 10/2005 | Malave et al. |
| 2005/0238507 A1 | 10/2005 | Dilanni et al. |
| 2005/0245799 A1 | 11/2005 | Brauker et al. |
| 2005/0273076 A1 | 12/2005 | Beasley et al. |
| 2005/0276705 A1* | 12/2005 | Pinkerton ................ F04B 7/06 417/415 |
| 2005/0283144 A1 | 12/2005 | Shiono et al. |
| 2006/0041229 A1 | 2/2006 | Garibotto et al. |
| 2006/0074381 A1 | 4/2006 | Malave et al. |
| 2006/0122577 A1 | 6/2006 | Poulsen et al. |
| 2006/0129090 A1 | 6/2006 | Moberg et al. |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0200073 A1 | 9/2006 | Radmer et al. |
| 2006/0263839 A1 | 11/2006 | Ward et al. |
| 2006/0264835 A1 | 11/2006 | Nielsen et al. |
| 2006/0282290 A1 | 12/2006 | Flaherty et al. |
| 2007/0016149 A1 | 1/2007 | Hunn et al. |
| 2007/0021733 A1 | 1/2007 | Hansen et al. |
| 2007/0049865 A1 | 3/2007 | Radmer et al. |
| 2007/0060894 A1 | 3/2007 | Dai |
| 2007/0073229 A1 | 3/2007 | Gorman et al. |
| 2007/0073559 A1 | 3/2007 | Stangel |
| 2007/0088244 A1 | 4/2007 | Miller et al. |
| 2007/0088271 A1 | 4/2007 | Richards |
| 2007/0118405 A1 | 5/2007 | Campbell et al. |
| 2007/0191702 A1 | 8/2007 | Yodfat et al. |
| 2008/0004515 A1 | 1/2008 | Jennewine |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051710 A1 | 2/2008 | Moberg et al. |
| 2008/0051711 A1 | 2/2008 | Mounce et al. |
| 2008/0051714 A1 | 2/2008 | Moberg et al. |
| 2008/0051716 A1* | 2/2008 | Stutz ............... A61M 5/1413 604/151 |
| 2008/0051718 A1 | 2/2008 | Kavazov et al. |
| 2008/0051727 A1 | 2/2008 | Moberg et al. |
| 2008/0051730 A1 | 2/2008 | Bikovsky |
| 2008/0051738 A1 | 2/2008 | Griffin |
| 2008/0051765 A1 | 2/2008 | Mounce |
| 2008/0086111 A1 | 4/2008 | Cowan |
| 2008/0097321 A1 | 4/2008 | Mounce et al. |
| 2008/0097326 A1 | 4/2008 | Moberg et al. |
| 2008/0097327 A1 | 4/2008 | Bente et al. |
| 2008/0097328 A1 | 4/2008 | Moberg et al. |
| 2008/0097375 A1 | 4/2008 | Bikovsky |
| 2008/0097381 A1 | 4/2008 | Moberg et al. |
| 2008/0114305 A1 | 5/2008 | Gerondale |
| 2008/0116647 A1 | 5/2008 | Anderson et al. |
| 2008/0119707 A1 | 5/2008 | Stafford |
| 2008/0132842 A1 | 6/2008 | Flaherty |
| 2008/0147041 A1 | 6/2008 | Kristensen |
| 2008/0160492 A1 | 7/2008 | Campbell et al. |
| 2008/0187449 A1* | 8/2008 | Breidenbach ............. F04B 7/06 417/499 |
| 2008/0194924 A1 | 8/2008 | Valk et al. |
| 2008/0215006 A1 | 9/2008 | Thorkild |
| 2008/0261255 A1 | 10/2008 | Tolosa et al. |
| 2008/0264261 A1 | 10/2008 | Kavazov et al. |
| 2008/0269680 A1 | 10/2008 | Ibranyan et al. |
| 2008/0269713 A1 | 10/2008 | Kavazov |
| 2008/0294028 A1 | 11/2008 | Brown |
| 2008/0306434 A1 | 12/2008 | Dobbles et al. |
| 2008/0312608 A1 | 12/2008 | Christoffersen et al. |
| 2009/0005724 A1 | 1/2009 | Regittnig et al. |
| 2009/0005728 A1 | 1/2009 | Weinert et al. |
| 2009/0012472 A1 | 1/2009 | Ahm et al. |
| 2009/0048563 A1 | 2/2009 | Ethelfeld et al. |
| 2009/0062767 A1 | 3/2009 | Van Antwerp et al. |
| 2009/0062778 A1 | 3/2009 | Bengtsson et al. |
| 2009/0076453 A1 | 3/2009 | Mejlhede et al. |
| 2009/0112155 A1* | 4/2009 | Zhao ................ A61M 5/14212 604/67 |
| 2009/0149743 A1 | 6/2009 | Barron |
| 2009/0204077 A1 | 8/2009 | Hasted et al. |
| 2009/0221971 A1 | 9/2009 | Mejlhede et al. |
| 2009/0254037 A1* | 10/2009 | Bryant, Jr. ............. A61M 5/142 604/151 |
| 2009/0326472 A1* | 12/2009 | Carter ............... A61M 5/14216 604/180 |
| 2010/0049127 A1* | 2/2010 | Haueter ................ F04B 53/162 604/131 |
| 2011/0021990 A1* | 1/2011 | Navarro ............ A61M 5/14216 604/151 |
| 2011/0021993 A1* | 1/2011 | Bar-Haim ......... A61M 5/14216 604/153 |
| 2011/0054400 A1 | 3/2011 | Chong et al. |
| 2011/0230838 A1 | 9/2011 | Adams |
| 2013/0017099 A1* | 1/2013 | Genoud ............ A61M 5/14216 417/53 |
| 2013/0060194 A1* | 3/2013 | Rotstein ............ A61M 5/14566 604/151 |
| 2014/0170003 A1 | 6/2014 | Bergman et al. |

FOREIGN PATENT DOCUMENTS

| | | |
|---|---|---|
| EP | 2019206 A1 | 1/2009 |
| EP | 2187104 A1 | 5/2010 |
| JP | 2003509133 | 3/2003 |
| JP | 2004503303 | 2/2004 |
| JP | 2004524869 | 8/2004 |
| JP | 2005520646 | 7/2005 |
| JP | 2006526467 | 11/2006 |
| WO | 93/20864 A1 | 10/1993 |
| WO | WO 9934212 | 7/1999 |
| WO | WO 03074121 | 9/2003 |
| WO | WO 2004032994 | 4/2004 |
| WO | 2005/039674 A1 | 5/2005 |
| WO | WO 2007051139 | 5/2007 |
| WO | WO 2008040812 | 4/2008 |
| WO | WO 2009004627 | 1/2009 |
| WO | WO 2009021039 | 2/2009 |
| WO | WO 2009021052 | 2/2009 |
| WO | WO 2012069308 | 5/2012 |
| WO | WO 2012126744 | 9/2012 |

* cited by examiner

INTERNAL CAM METERING PUMP

BACKGROUND OF THE INVENTION

1. Field of the Invention

The present invention is directed to a micropump adapted for the continuous delivery of a liquid medication by infusion such as may be used in the delivery of insulin for the treatment of diabetes.

2. Description of the Related Art

Micropumps for the subcutaneous delivery of drugs are known, for example, from U.S. Pat. Nos. 7,726,955 and 8,282,366. This prior art describes, in various embodiments, a pump having a rotor mounted in a stator, or housing. Sealing rings situated at an angle on axial extensions on the rotor cooperate with channels formed between the rotor and the stator to move liquid in precise amounts through a rotor housing. However, these embodiments are relatively complex and not cost effective. The user keeps the pump when the infusion patch is changed, for several weeks. As the art continues to evolve toward fully disposable pumps, the need for compact and economical micropump designs remains acute.

Another infusion pump known in the prior art comprises a rigid reservoir with a lead screw engaged in the reservoir to dispense medication through the cannula as the lead screw advances. In this arrangement, the actuator for delivery of the medication is directly connected to the lead screw and must therefore be very precise. Moreover, the device requires the rigid reservoir to provide calibrated dosages. Thus it is impossible to use a flexible reservoir, and the number of possible layouts for the pump is limited.

SUMMARY OF THE INVENTION

In one aspect, the present invention is a micropump for delivery of medication by infusion, comprising: a pump housing; a piston positioned in the pump housing having a longitudinal piston axis; and a motor adapted to rotate the piston about the piston axis. The pump housing has an axial opening receiving the piston, a first aperture positioned radially with respect to the piston axis in fluid communication with a reservoir, and a second aperture radially positioned with respect to the piston axis in fluid communication with a cannula. The piston has an eccentric cam surface at one end thereof, said cam surface adapted to open and close the first aperture and the second aperture at respective rotational positions of the piston. The axial position of the piston inside the pump housing determines a pump volume space.

In embodiments, the pump housing is stationary and the piston comprises an axial position cam surface, between the motor and the eccentric cam surface, engaging a stationary member on the pump housing, adapted to translate the piston axially within the pump housing when the piston rotates.

In another aspect, the invention is a method for delivering medication by infusion with the above-described pump, including the steps of providing instructions to a microprocessor to deploy the cannula, and to cause the piston to rotate, drawing a volume of medication into the pump volume space from the reservoir and expelling the volume of medication through the cannula for infusion to a patient. In embodiments, the medication is insulin and the infusion dosage comprises an infusion over one to five days, and the method further comprises disposing of the pump after delivery of the infusion dosage.

DETAILED DESCRIPTION OF THE INVENTION

Figure 1:
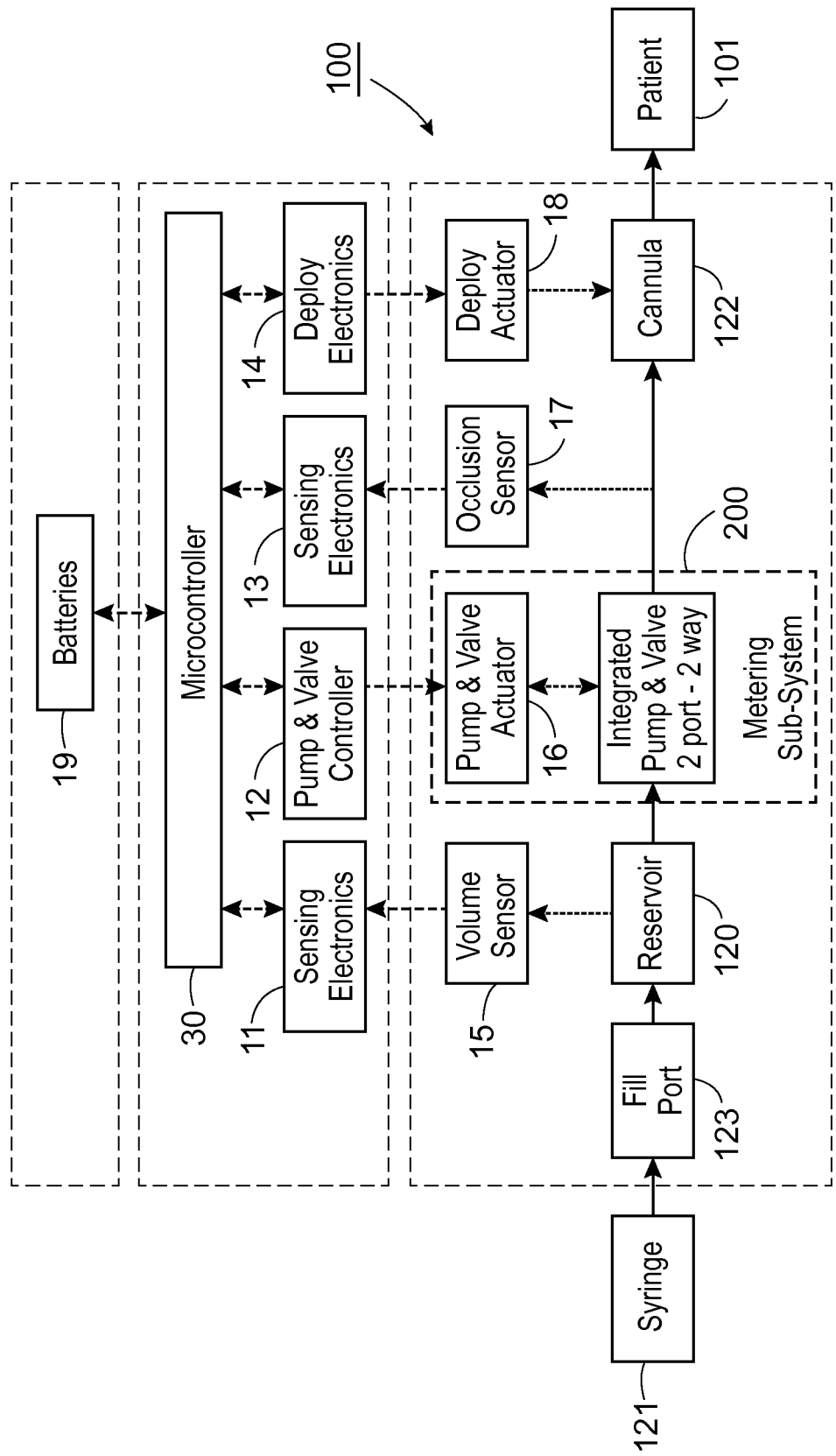
FIG. 1 is a schematic overview of the fluid metering and delivery systems according to the invention.
Figure 2:
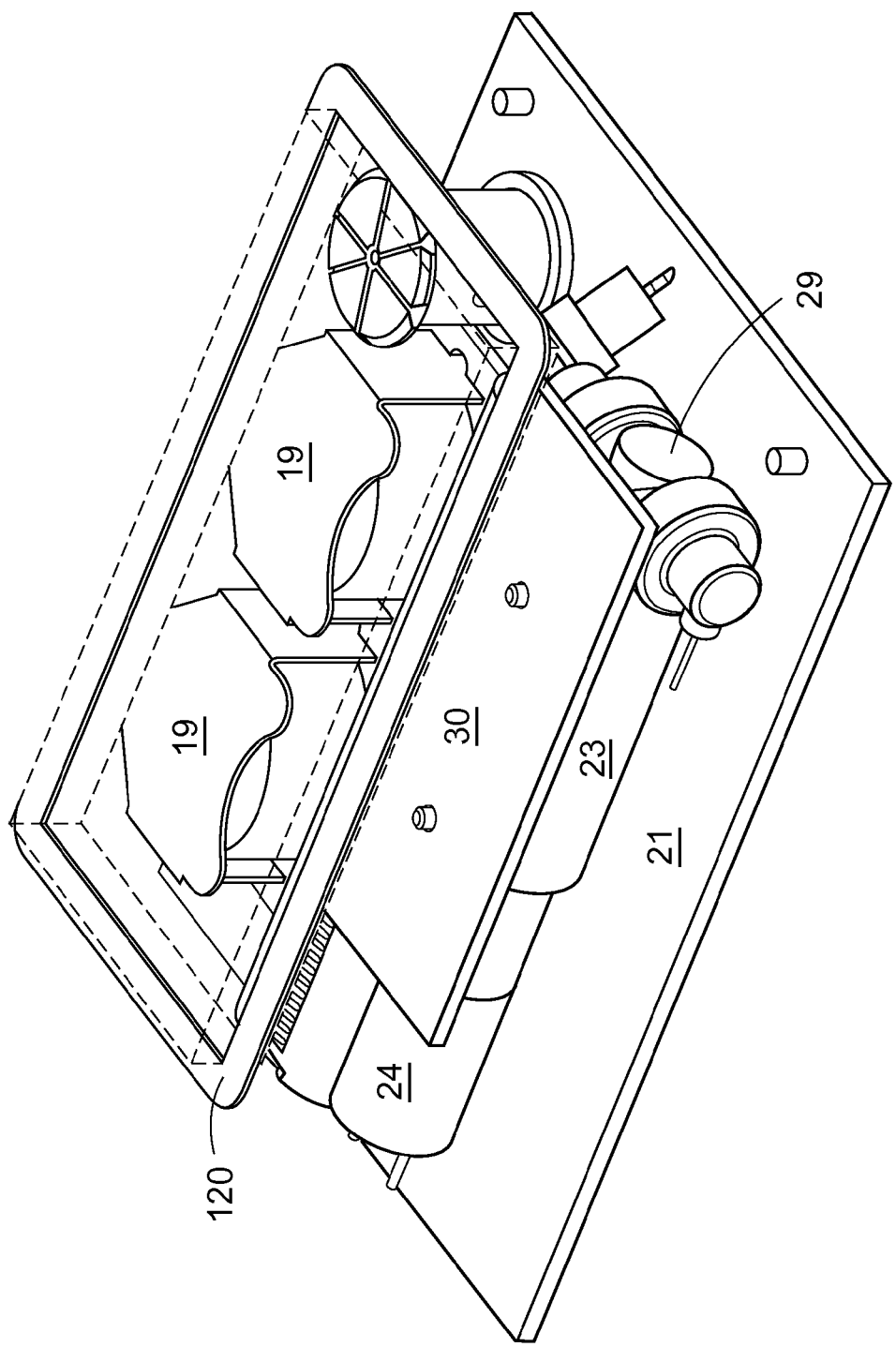
FIG. 2 is a view of the assembled fluid metering and delivery systems.

FIG. 1 provides a schematic overview of a fluid delivery system 100, comprising a reservoir 120 in fluid communication with metering subsystem 200 for drawing a precise amount of fluid from the reservoir. A cannula mechanism 122 is provided for delivering medication from the metering subsystem 200 to the user 101. The fluid delivery system, including metering subsystem 200, is preferably lightweight and wearable and assembled in a compact form as shown in FIG. 2, so that the elements may be included in a single housing. The cannula mechanism 122 may be connected to the infusion site by an infusion set comprising tubing and a patch, or alternatively a cannula insertion mechanism may be incorporated into the housing along with the metering subsystem 200.

In embodiments, the pump is adapted to provide a continuous infusion dosage over 1 to 5 days. For example, in the case of insulin infusion, the pump may be worn and disposed of after 84 hours and the reservoir is sized to provide a dosage regimen in basal and bolus segments as a time varying series of fixed volume pulses. The infusion profile is split between the basal and bolus segments. For example, the basal segment may be a quasi-continuous flow of 5 µl pulses with a time lag that ranges from 0.17 to 1.2 hours/pulse, while the bolus segments comprise discrete volumes that generally occur around meal times, typically in a range of 10 to 500 µl, delivered at the maximum pump flow rate (minimum pump cycle time). In the case of insulin infusion, the reservoir 120 may be adapted to hold 1 ml to 5 ml of medication, preferably about 3 ml. However, this value is not critical. Although the invention is not limited to any specific reservoir embodiment, the reservoir 120 is preferably flexible and is not engaged with a plunger and lead screw, as is the case with many prior art insulin pumps. The flexible reservoir does not have an internal actuator mechanism for delivering fluid, which permits the overall pump to have a smaller footprint and more compact design. A suitable flexible reservoir may comprise a pouch made of medical grade flexible polyvinylchloride (PVC) or the like. Alternatively, a single rigid wall of medical grade plastic may be bonded to a flexible wall to form the reservoir. Reservoir 120 may be filled via a fill port 123 by syringe 121, for example, or a prefilled reservoir or cartridge may be used. Metering subsystem 200 may be configured in fluid communication with the fill port 123, so that metering subsystem 200 can be used to fill the reservoir 120 from an external source of medication via fill port 123.

Microcontroller 30 is provided on a printed circuit board (PCB) or the like and interfaces with sensors and circuitry 11, 12, 13, 14, 15, 17 and with actuators 16 and 18, to control the pump and cannula. As illustrated in FIG. 1, sensor 17 is an occlusion sensor or more generally an error condition sensor. Power is provided by one or more batteries 19 in the housing. Display and user operable controls (not shown) may be provided on the unit, operatively connected to the PCB, or on a remote programming unit, to set and initiate basal and bolus segments of the dosage, as is known in the prior art.

The embodiment of the metering system according to the invention depicted in the figures comprises a positive displacement pump with integrated flow control valves and a mechanical actuator and drive system. In the embodiment shown in FIG. 2, the actuator is a DC gear motor 24 powered by batteries 19, however, other motor systems may be adapted for use with the invention, including a solenoid, nitinol (nickel-titanium alloy) wire motor, voice coil actuator motor, piezoelectric motor, or wax motor. The elements are arranged on support 21 received in a housing (not shown) to be worn on the patient's body.

Figure 3:
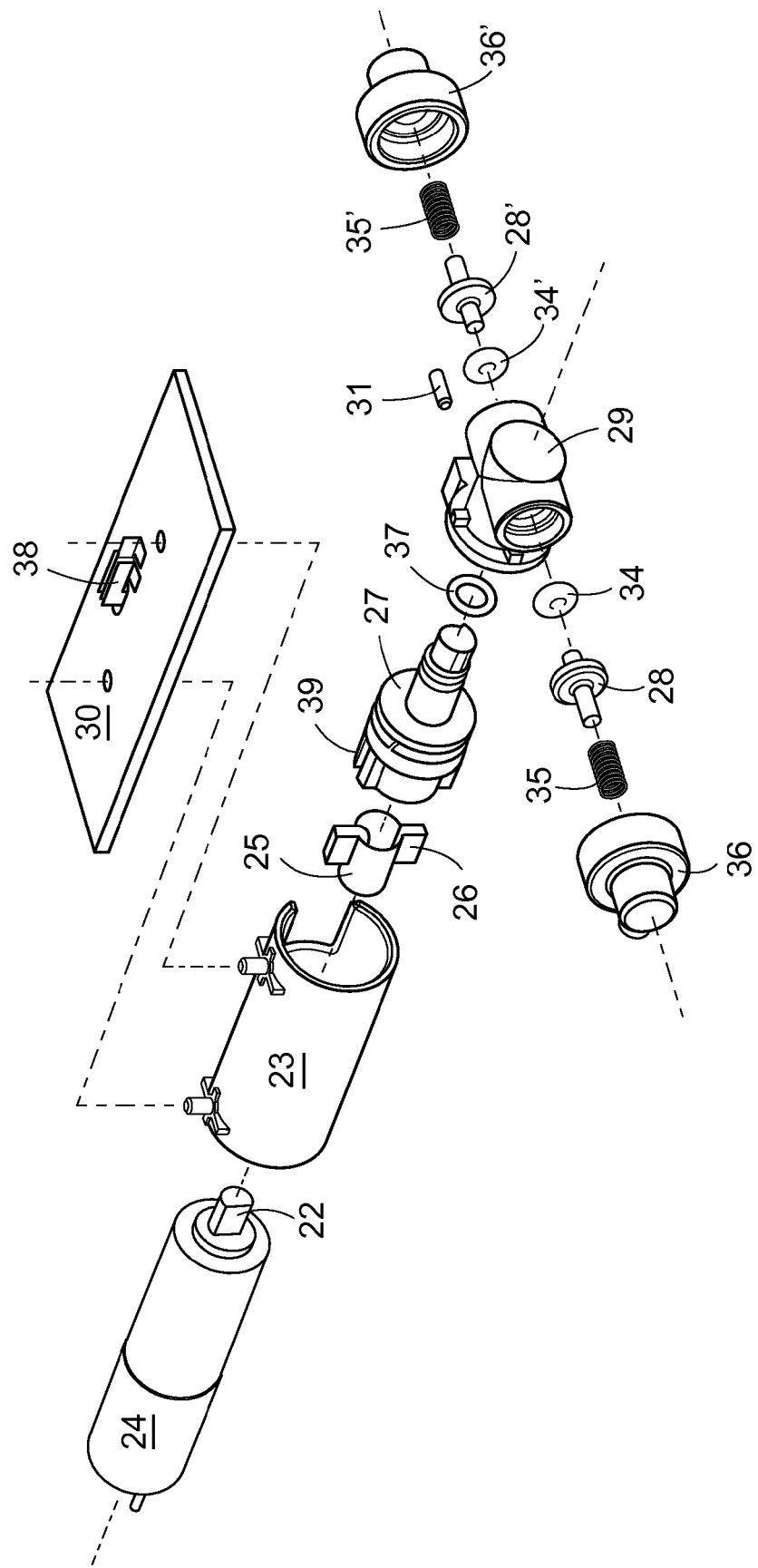
FIG. 3 is an exploded view of the fluid metering system.

As shown in the exploded view of FIG. 3, the motor 24 is received in stationary motor casing 23. Connector 25 receives the motor shaft 22 of the motor 24 and transmits torque from the motor to pump piston 27. As used herein, the "axial" direction is along the axis of the motor shaft and the "radial" direction is the perpendicular direction. Unless the context clearly requires otherwise, the "clockwise" direction means clockwise looking down the axis of the motor shaft toward the motor. Slots 39 on piston 27 receive tabs 26 on connector 25 so that piston 27 rotates in unison with the motor shaft, but remains free to move axially. Alternatively, the piston may have rotational freedom but an axially fixed position, and the pump housing may be rotationally fixed but connected to the piston to allow for axial translation. In either case, the pump volume is determined by the axial position of a piston within the pump housing.

Figure 4A:
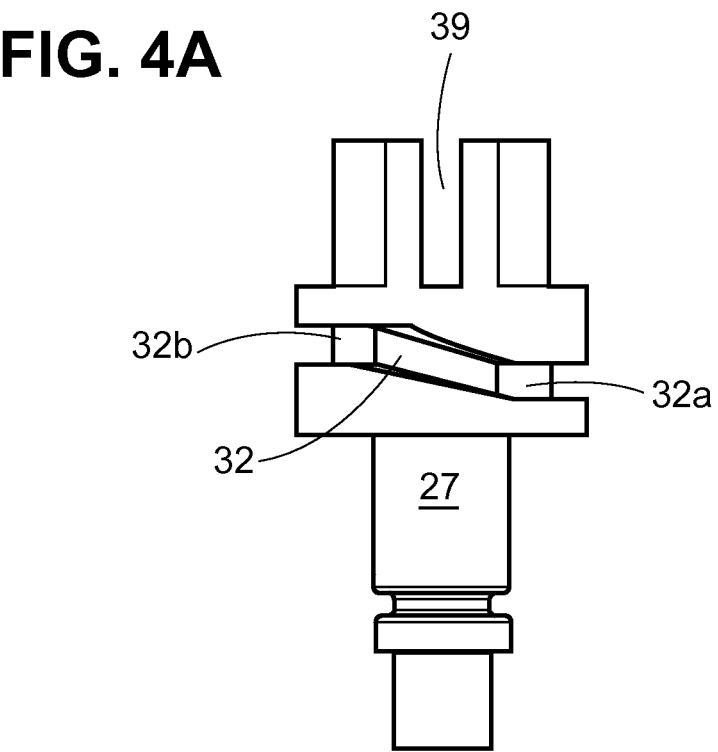
FIG. 4A and FIG. 4B are top and end views of the pump piston element of the fluid metering system.

In the embodiment shown, pump piston 27 is received in an axial opening in a stationary pump housing 29 and encloses pump volume space 47 in the pump housing behind elastomeric seal 37. As shown in FIG. 4A, piston 27 is configured with an axial position cam surface 32. As described below, axial cam surface 32 engages a member on stationary pump housing 29 and causes piston 27 to translate axially within housing 29 when motor shaft 22 rotates. For example, in the embodiment shown, the member engaging the cam surface is a pin 31 inserted through the pump housing.

The metering subsystem 200 is adapted to pull a precise volume of fluid from flexible reservoir 120 into pump volume 47, and then expel the fluid through cannula 122 to an infusion site in small, discrete doses. A suitable pump volume space 47 may have a volume of 1 µl to 10 µl, preferably about 5 µl, so that two rotations of pump piston 27 deliver a unit (U) of insulin. Importantly, the position of pump piston 27 inside pump housing 29 determines the stroke, and the internal diameter of the pump housing determines the nominal size and accuracy of the dose. Therefore dosage accuracy is not determined by a specific rotational position of the motor shaft to deliver a corresponding amount of medication and the start/stop point for the rotational pump cycle need not be precise. The pump volume 47 may be altered by changing the diameter of piston 27 and/or pump housing 29. In embodiments, cannula deployment is triggered by rotation of motor 24, in a one-step deployment and infusion operation.

Figure 4B:
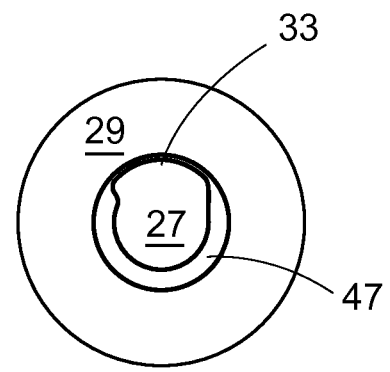
Figure 5:
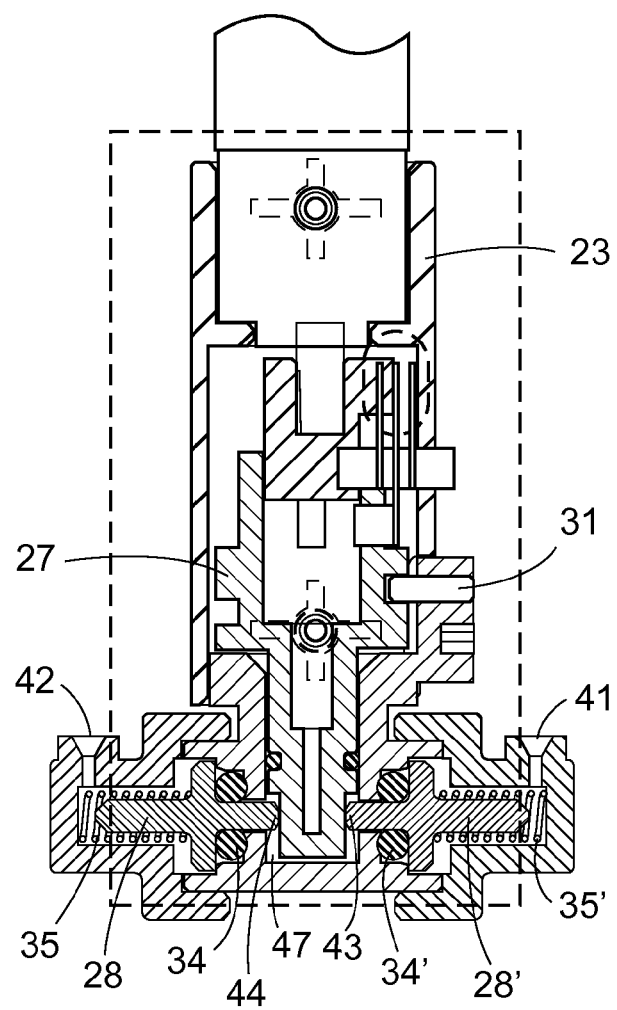
FIG. 5 and FIG. 6 are cross sectional views of the metering system.
Figure 6:
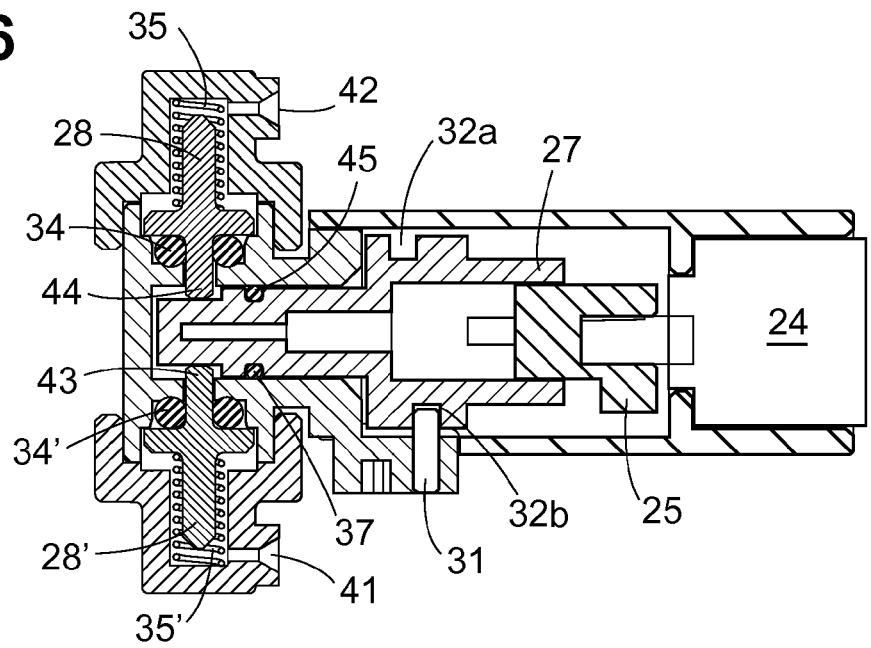

In order to pull fluid into pump volume 47 during the intake stroke, and expel fluid during the discharge stroke, piston 27 is provided with an eccentric cam surface 33, as shown in FIG. 4B, to actuate valves to sequentially open and close reservoir fluid port 42 and cannula fluid port 41 at each end of the pump stroke to ensure that fluid flow is unidirectional from the reservoir to the patient and that there is no possibility of flow from the patient to the reservoir. As shown in the cross-sectional view of FIG. 5, the pump housing is provided with first and second apertures 44, 43 positioned radially with respect to the pump piston axis. First aperture provides fluid communication between pump volume 47 and reservoir port 42, while second aperture 43 provides fluid communication between pump volume 47 and cannula port 41. In this embodiment, apertures 43, 44 are positioned on opposite sides of pump housing 29, 180 degrees apart with respect to piston 27. The angular allocation for each segment of the pump cycle may be adjusted as needed to optimize performance of the pump, by altering the size and slope of the eccentric cam surface 33, to increase or decrease the angular allocation for a particular portion of the pump cycle, or by changing the radial position of apertures 43, 44.

In the embodiment shown, the first and second apertures 44, 43 each receive a valve structure. Each valve structure includes respective O-ring seal 34, 34' surrounding the aperture and a respective valve actuator 28, 28' which compresses a respective O-ring seal 34, 34' under force of respective spring 35, 35' to close the respective aperture 43, 44 when cam surface 33 is not pressing against actuator 28, 28'. When cam surface 33 is rotated into position and depresses a valve actuator 28 or 28', the fluid line to the cannula port 41 or reservoir port 42 is opened. The springs 35, 35' are maintained in a biased state in the valve seat by respective valve caps 36, 36' and must ensure sufficient spring force to prevent back flow at back pressures encountered during use of the device. Although O-rings are depicted in this embodiment, other sealing systems known in the art could be adapted for this purpose, such as an elastomeric ball in a V-shaped seat, an overmolded V-shaped poppet, or an overmolded membrane which can be biased to provide fluid entry through apertures 43, 44. In general, components of the metering subsystem are made of a rigid medical grade plastic, such as acrylonitrile butadiene styrene (ABS) for all of the pump components, while liquid silicone rubber (LSR) with shore A hardness between 20 and 50 is used for the seals. If desired, the LSR seals may be molded directly onto the hard plastic substrates, in which case the substrate parts should be made of a plastic material with a higher softening temperature such as polyetherimide (PEI) or polysulfone (PS).

In the embodiment depicted, pump housing 29 is stationary and piston 27 is translated inside the pump housing 29. For this purpose, piston 27 comprises an axial position cam surface in the form of a groove 32. As seen in FIG. 4A, groove 32 includes proximal ledge 32b located toward the motor 24 and a distal ledge 32a located toward eccentric cam surface 33 on the opposite end of piston 27 from motor 24. A stationary member, such as pin 31, is received through an opening in the pump housing and constrains the piston to move axially back and forth between the position of proximal ledge 32b and axial ledge 32a, guided along an axial translation portion of the groove 32, as motor shaft 22 rotates. One of ordinary skill in the art will appreciate that an axial cam surface on piston 27 engaging pump housing 29 may be embodied in various ways to provide for axial movement of piston 27. For example, a groove may be located on the pump housing instead of on the piston.

A complete pump cycle requires 360 degrees of rotation in one direction. Rotating motor shaft 22 in the reverse direction will cause fluid to flow in the opposite direction. In embodiments, the pump may be placed in fluid communication with fill port 123 to fill reservoir from an external source such as a vial by rotating the motor shaft in the reverse direction.

The pump cycle will be described with reference to a complete clockwise rotation (viewed looking down the piston toward the motor). The rotation of eccentric cam surface 33 about the piston axis, accompanied by the reciprocating action of piston 27 in this embodiment is understood by referring to the following sequential steps of the pump cycle described in FIG. 7 through FIG. 13: (1) reservoir valve open state, (2) pump intake stroke; (3) reservoir valve closed state; (4) cannula valve open state; (5) pump discharge stroke; and (6) cannula valve closed state.

Figure 7:
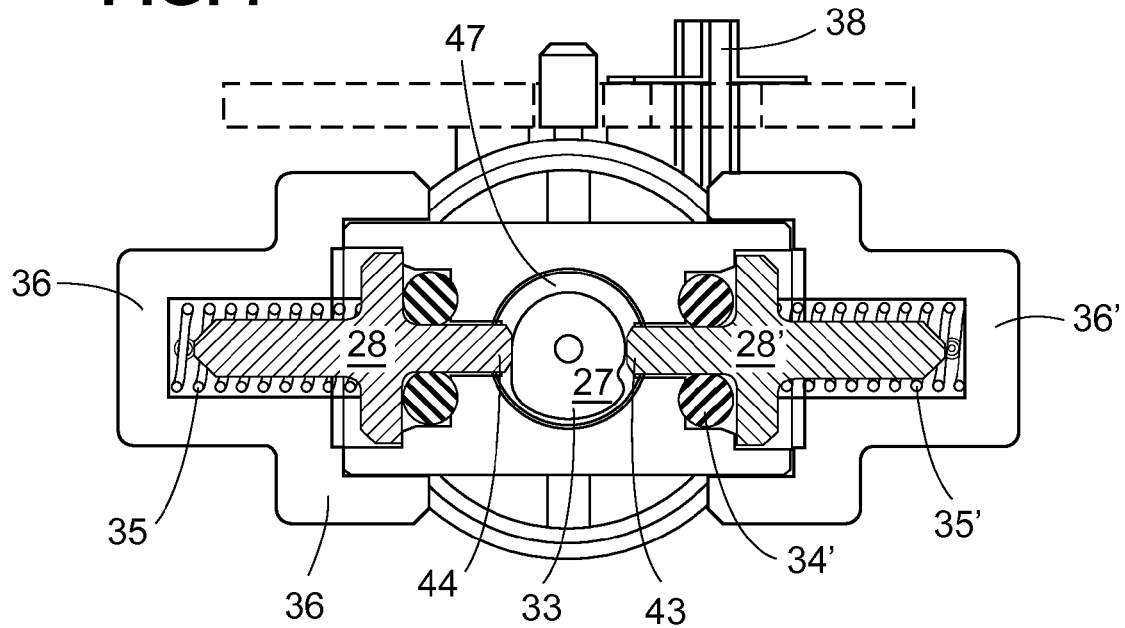
FIG. 7 is a cross sectional view of the pump housing in the starting position of the pump cycle.
Figure 7A:
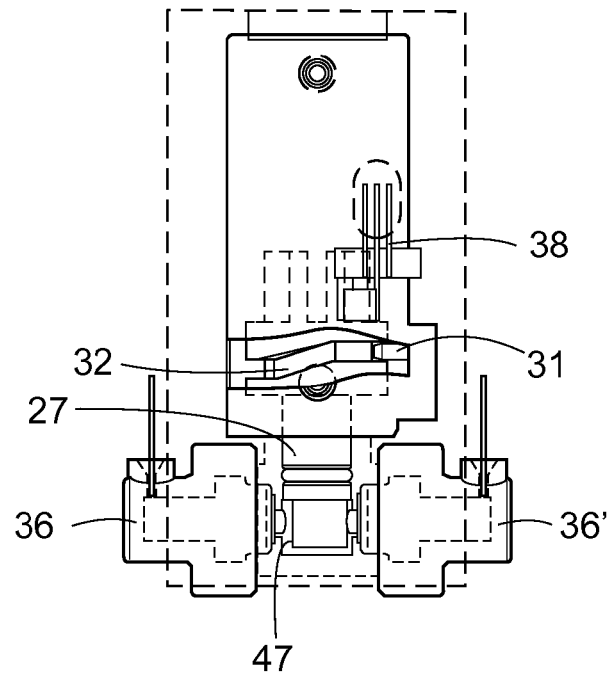
FIG. 7A and FIG. 7B are corresponding partial cutaway views of the fluid delivery system in the stage depicted in FIG. 7, from different angles.
Figure 7B:
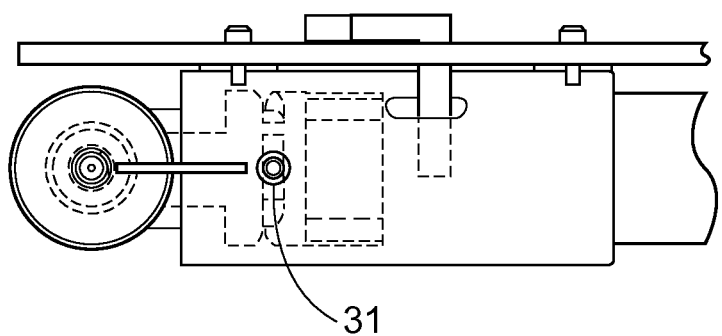

FIG. 7 is a cross sectional view from the end of the pump housing, looking down the piston toward the motor, showing the metering system in its starting position. The pump piston 27 is fully extended. As shown in FIG. 7A and FIG. 7B, pin 31 rests on proximal ledge 32b in this position and the piston does not translate axially. Cam surface 33 is not engaged with either valve actuator 28 or 28', and a slight clearance is provided between cam surface 33 and actuators 28 and 28' on radially opposite sides of the pump housing. The cam surface 33 is said to be "in clearance" with the actuator tips in this state. In this state, the valves are closed by the force of springs acting on O-ring seals 34, 34' through valve actuators 28 and 28'. In the initial state, valve actuators 28 and 28' are spring loaded against valve caps 36 and 36' so that they have a permanent bias sufficient to prevent leakage at the operating back pressures of the device. The valve actuator may rest on a shoulder in the pump housing around apertures 43, 44. In this way, compression of O-ring seals 34 or 34' is determined by the geometry of the valve actuator cooperating with the surfaces of the pump housing around the apertures 43, 44, rather than solely on the spring force.

Figure 8:
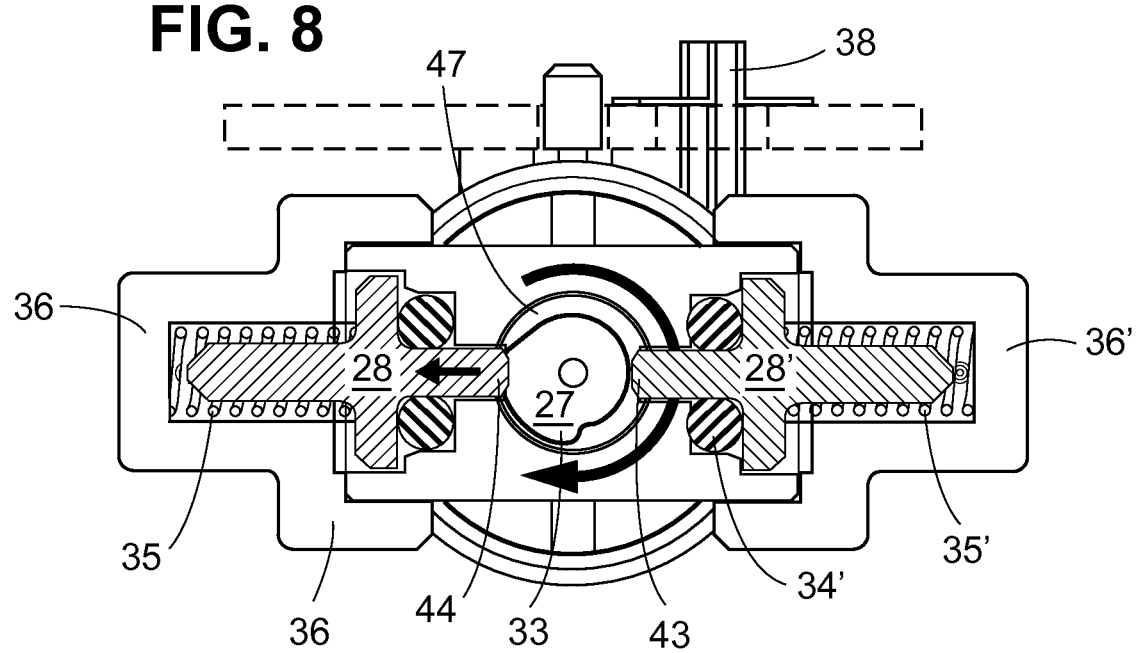
FIG. 8 is a cross sectional view of the pump housing in the early stages of a pump cycle, before the start of the intake stroke.

FIG. 8 depicts the reservoir valve open state (1) before the start of the intake stroke. Motor 24 is shown rotating in a clockwise direction so that cam surface 33 on piston 27 rotates to contact valve actuator 28 to bias spring 35 and open fluid communication with reservoir port 42. In this position, pin 31 has not yet entered the sloped axial translation portion of groove 32.

Figure 9:
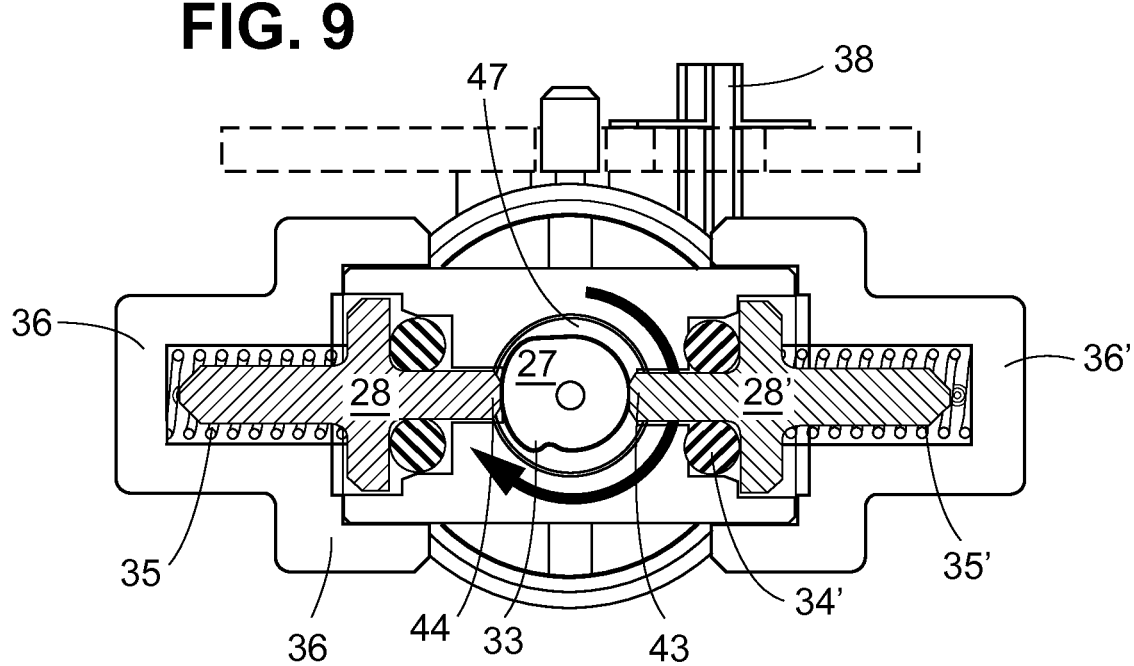
FIG. 9 is a cross sectional view of the pump housing during the intake stroke.
Figure 9A:
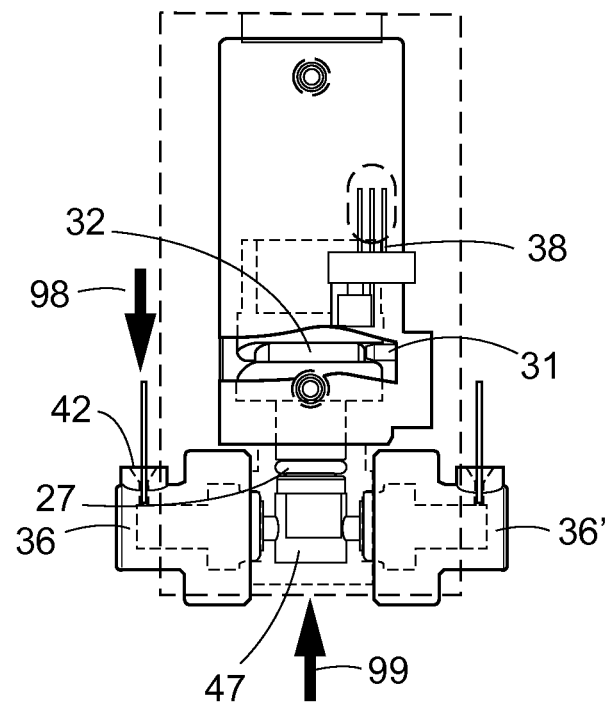
FIG. 9A and FIG. 9B are corresponding partial cutaway views from different angles.
Figure 9B:
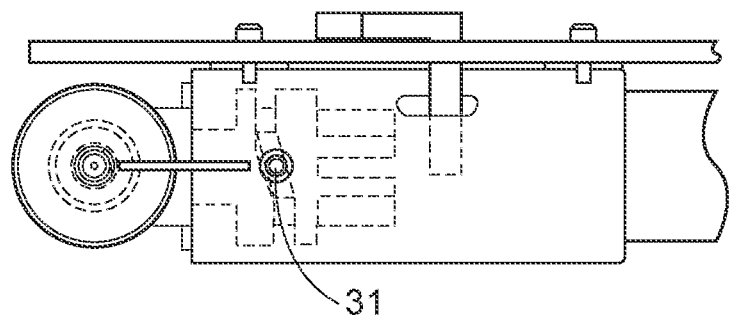

During the pump intake stroke (2) depicted in FIG. 9, FIG. 9A and FIG. 9B, actuator 28 is fully depressed. Fluid flows into the pump volume space 47 through reservoir port 42 and first aperture 44 while second aperture 43 remains closed. As shown in FIG. 9A and FIG. 9B, pin 31 engages the angled portion of axial cam surface 32 causing piston 27 to translate toward motor 24 in the direction indicated by arrow 99. Fluid is drawn into pump volume space 47 as indicated by arrow 98. The intake stroke is complete when pin 31 rests on distal ledge 32a, stopping axial movement of piston 27. Actuator 28 remains fully depressed and actuator 28' remains in clearance with cam surface 33.

Figure 10:
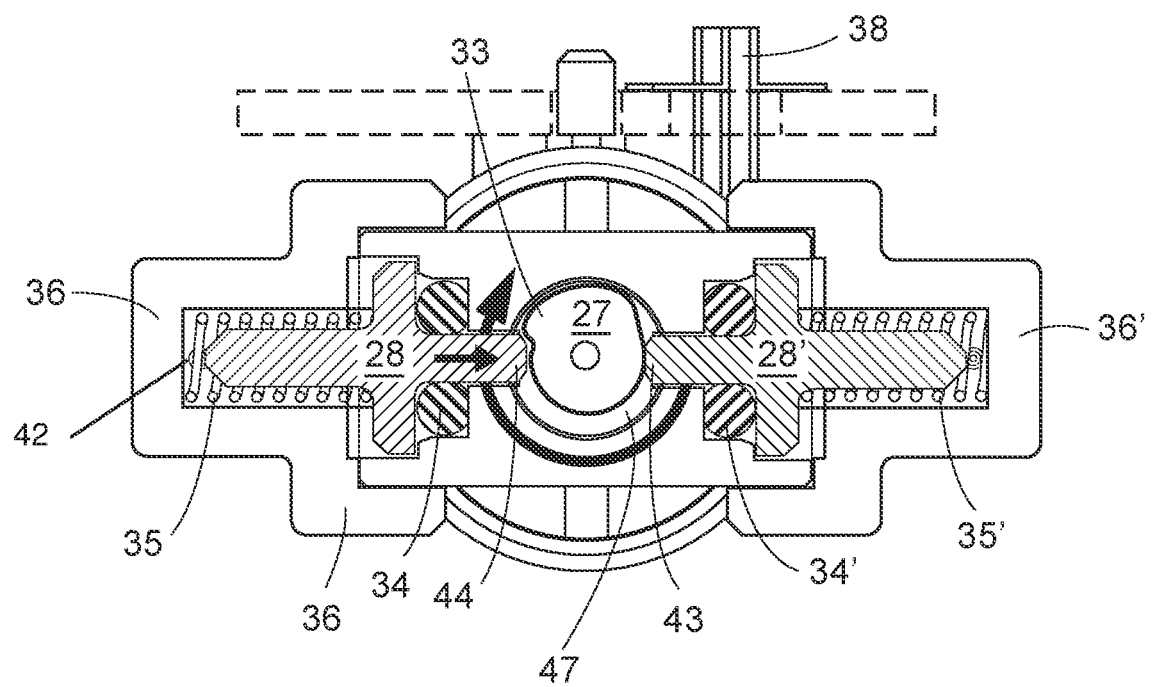
FIG. 10 is a cross sectional view of the pump housing after the intake stroke.
Figure 10A:
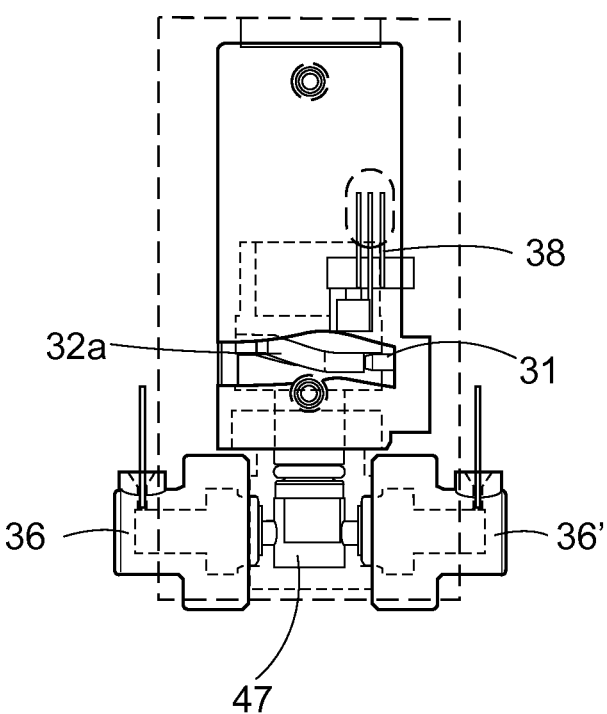
FIG. 10A and FIG. 10B are corresponding partial cutaway views from different angles.
Figure 10B:
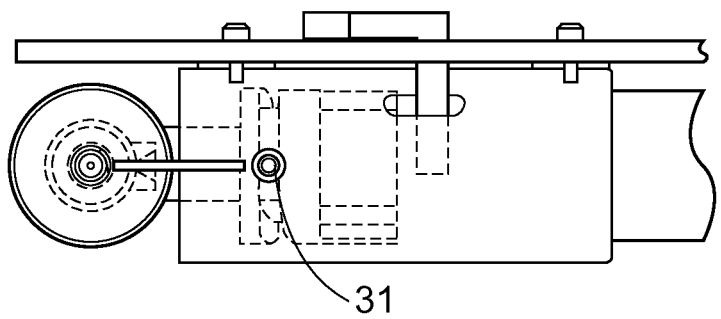

FIG. 10, FIG. 10A and FIG. 10B show reservoir port 42 closing. Rotation of piston 27 causes cam surface 33 to release actuator 28, recompressing seal 34 due to bias of spring 35 and stopping fluid flow through first aperture 44. During this portion of the pump cycle, pin 31 rests on distal ledge 32a preventing axial translation of piston 27.

Figure 11:
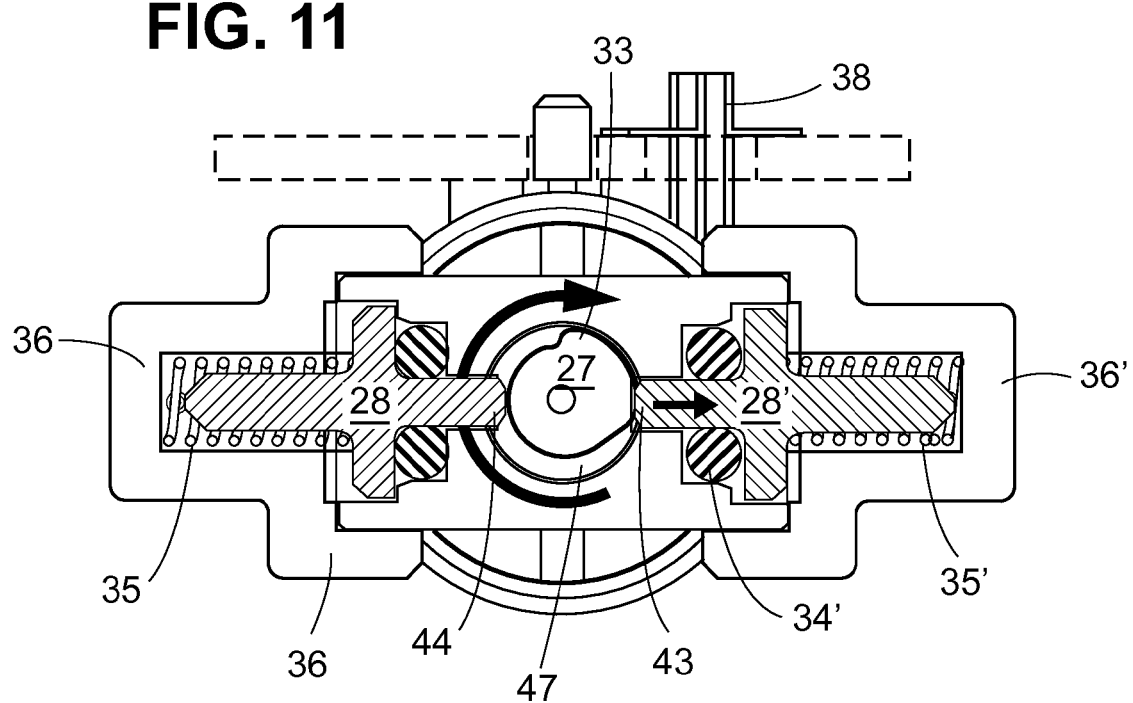
FIG. 11 is a cross sectional view of the pump housing prior to initiation of the discharge stroke.
Figure 11A:
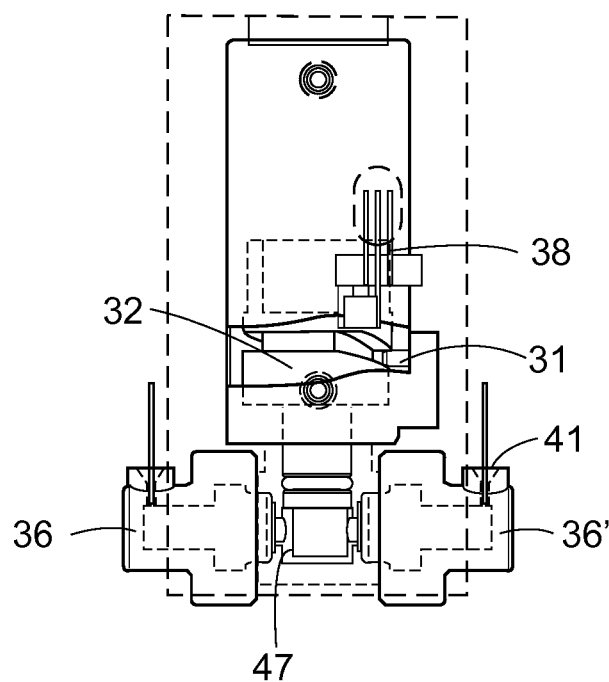
FIG. 11A and FIG. 11B are corresponding partial cutaway views from different angles.
Figure 11B:
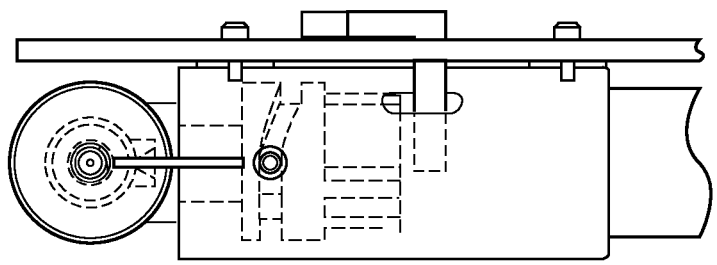

FIG. 11 shows cannula valve open state (4). Rotation of piston 27 causes cam surface 33 to engage actuator 28', releasing compression on O-ring seal 34' and opening fluid communication between pump volume 47 and cannula port 41 through second aperture 43. FIG. 11A and FIG. 11B show pin 31 resting on distal ledge 32a during this portion of the pump cycle, preventing axial translation of piston 27.

Figure 12:
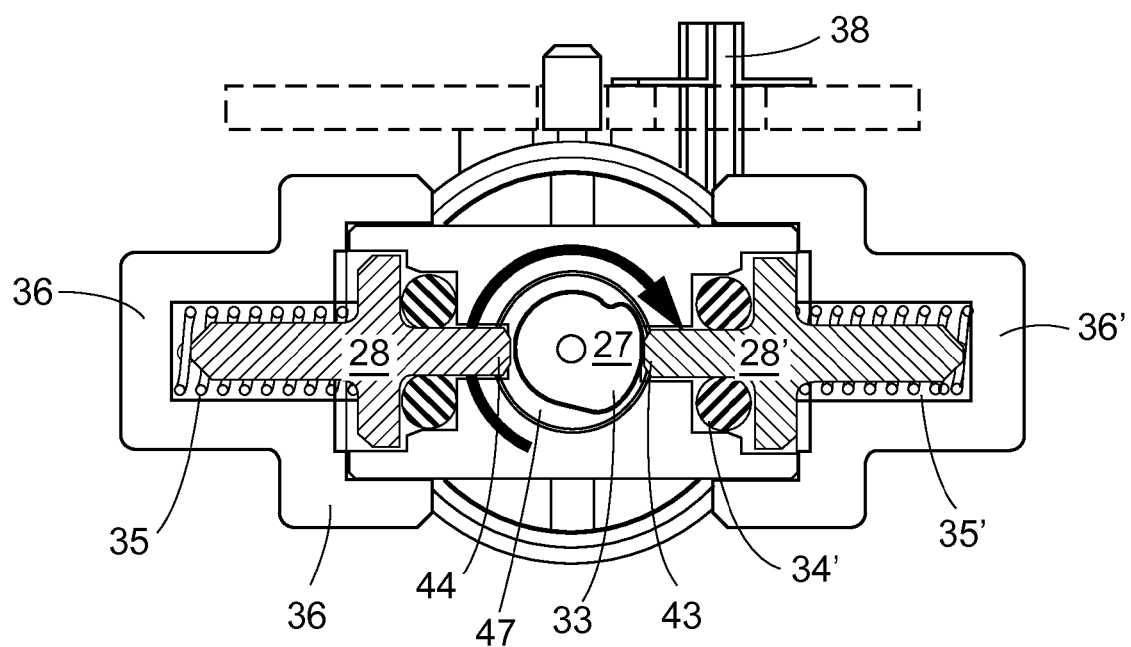
FIG. 12 is a cross sectional view of the pump housing during the discharge stroke.
Figure 12A:
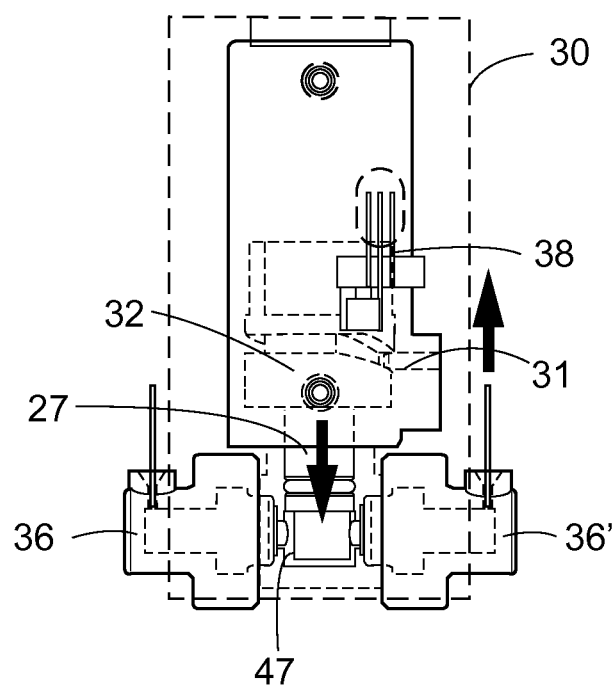
FIG. 12A and FIG. 12B are corresponding partial cutaway views of the fluid delivery system during the discharge stroke from different angles.
Figure 12B:
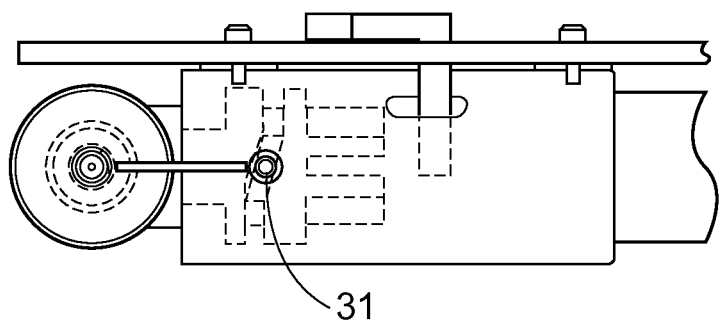

During the pump discharge stroke (5), depicted in FIG. 12, FIG. 12A, and FIG. 12B, eccentric cam surface 33 holds open fluid communication with the cannula port 41 while reservoir port 42 remains closed. FIG. 12A shows piston 27 moved axially in a distal direction as indicated by the arrow. Pin 31 engages the angled axial translation portion of cam surface 32, as shown in FIG. 12B, causing piston 27 to translate away from motor 24 and causing fluid to be discharged from pump volume space 47 through cannula port 41 as indicated by the arrow.

Figure 13:
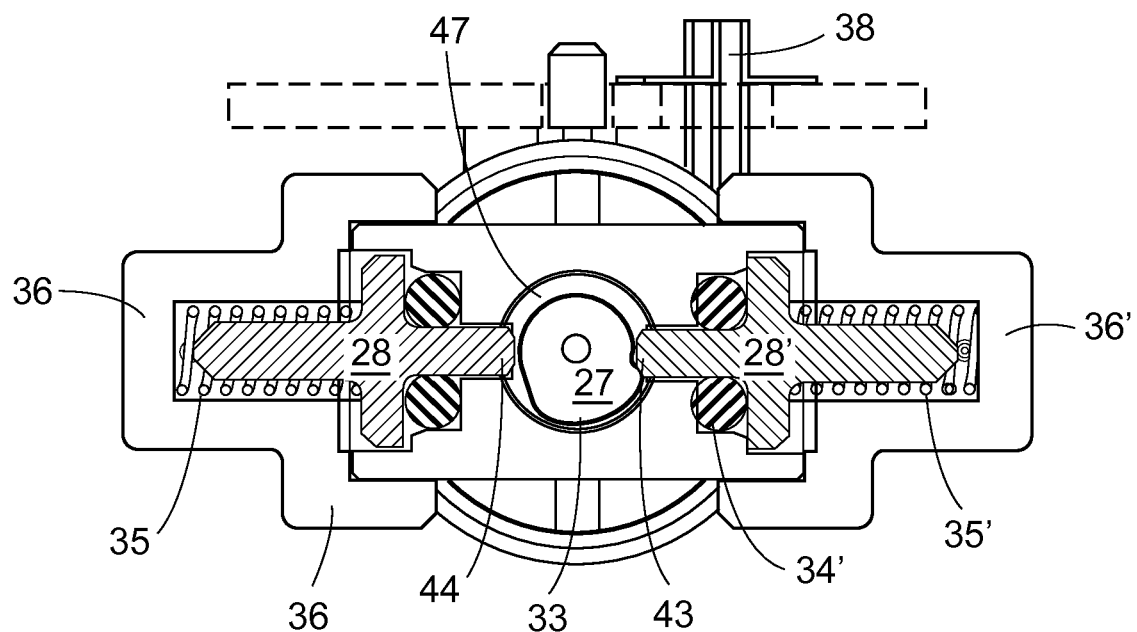
FIG. 13 depicts the rotational position of the piston at the end of the pump cycle.

After the piston has completed 360 degrees of rotation, as depicted in FIG. 13, travel sensor 38 is engaged, indicating that the pump cycle is complete. With the pump returned to the cannula valve closed state (6), reservoir port 42 and cannula port 41 are blocked and pin 31 rests on proximal ledge 32b. In the embodiment shown, travel sensor 38 is an ON/OFF switch that detects that the pump has completed a full cycle. However, other sensor systems, such as an encoder wheel and optical sensor, may be used to recognize intermediate states and communicate that information to microprocessor 30. The use of a higher resolution sensor permits the discharge stroke to be incremented. In the embodiment described herein, the discharge stroke includes a complete rotation of piston 27, emptying the contents of pump volume 47, however, a finer resolution of infusion dosage could be implemented without departing from the scope of the invention.

The foregoing description of the preferred embodiments is not to be deemed limiting of the invention, which is defined by the appended claims. The person of ordinary skill in the art, relying on the foregoing disclosure, may practice variants of the embodiments described without departing from the scope of the invention claimed. For example, although described in connection with continuous delivery of insulin for treatment of diabetes, it will be apparent to those of skill in the art that the infusion pump could be adapted to deliver other medications. A feature or dependent claim limitation described in connection with one embodiment or independent claim may be adapted for use with another embodiment or independent claim, without departing from the scope of the invention.

What is claimed is:

1. A micropump for delivery of medication by infusion, comprising:
    a pump housing;
    a piston positioned in the pump housing having a longitudinal piston axis; and
    a motor adapted to rotate the piston about the piston axis;
    the pump housing having an axial opening receiving the piston, a first aperture positioned radially with respect to the piston axis and communicating with a reservoir, and a second aperture radially positioned with respect to the piston axis communicating with a cannula;
    the piston having an eccentric cam surface at one end thereof, said cam surface adapted to sequentially open and close the first aperture and the second aperture at respective rotational positions of the piston; wherein the axial position of the piston inside the pump housing determines a pump volume space;

wherein the first aperture and the second aperture each contain an O-ring seal and a spring loaded valve actuator, each valve actuator having a tip, the tips of both actuators being in clearance with the eccentric cam in a normally closed position, and a spring force on the seals being high enough to ensure that the valve actuators do not open under operating pressures of the micropump, wherein the eccentric cam sequentially biases each actuator upon rotation of the piston, releasing compression on the respective O-ring seals and permitting fluid flow through the first aperture and the second aperture, respectively.

2. The micropump according to claim 1, wherein the pump housing is stationary, and further comprising an axial position cam surface on the piston, between the motor and the eccentric cam surface, engaging a stationary member on the pump housing, and adapted to translate the piston axially within the pump housing when the piston rotates.

3. The micropump according to claim 2, wherein the stationary member on the pump housing is a cam pin received in an opening in the pump housing.

4. The micropump according to claim 1, wherein the piston is free to rotate but has a fixed axial position and wherein the pump housing is free to translate axially but has a fixed rotational position.

5. The micropump according to claim 1, further comprising a connecter between the motor and the piston, the connector transmitting torque between the motor and the piston, and engaging the piston to permit axial movement of the piston with respect to the connector and prohibit rotational movement of the piston with respect to the connector.

6. The micropump according to claim 5, wherein an axially elongated slot on the pump piston engages a tab on the connector to permit axial movement of the piston with respect to the connector and prohibit rotational movement of the piston with respect to the connector.

7. The micropump according to claim 1, further comprising a microprocessor, and a travel sensor having a contact switch communicating with the microprocessor triggered by rotation of the piston through a complete cycle.

8. The micropump according to claim 1, wherein the reservoir has at least one flexible wall.

9. The micropump according to claim 1, further comprising a microprocessor, a cannula deployment mechanism, a volume sensor in operative communication with the reservoir, a travel sensor in operative communication with the pump piston, and an error condition sensor in operative communication with a fluid line between the second aperture in the pump housing and the cannula, and wherein the motor, the cannula deployment mechanism, the volume sensor, the travel sensor and the error condition sensor are all in operative communication with the microprocessor.

10. A method for delivering medication to a patient by infusion with the pump according to claim 9, comprising the steps of providing instructions to the microprocessor to deploy the cannula, causing the piston to rotate, withdrawing a volume of medication into the pump volume space from the reservoir and expelling the volume of medication through the cannula for infusion of an infusion dosage to a patient.

11. The method according to claim 10, wherein the medication is insulin and the infusion dosage comprises an infusion over one to five days.

12. The method according to claim 11, further comprising the step of disposing of the pump after delivery of the infusion dosage.

13. The method according to claim 10, wherein the infusion dosage comprises a basal segment and at least one bolus segment.

14. The method according to claim 10, wherein the pump volume space is in a range of 1 µl to 10 µl and an infusion dosage is delivered by an integer number of rotations of the piston through 360 degrees.

15. The method according to claim 10, wherein the instructions provided to the microprocessor are programmed with user operable controls located on a wearable pump housing.

* * * * *